(12) United States Patent
Bozzacco

(10) Patent No.: US 7,258,876 B2
(45) Date of Patent: Aug. 21, 2007

(54) TOPICAL COMPOSITION FOR TREATING INFECTIOUS CONDITIONS OF SKIN AND MUCOSA

(76) Inventor: Craig Bozzacco, 7866 Spring Ave., Elkins Park, PA (US) 19027

( * ) Notice: Subject to any disclaimer, the term of this patent is extended or adjusted under 35 U.S.C. 154(b) by 391 days.

(21) Appl. No.: 10/357,964

(22) Filed: Feb. 5, 2003

(65) Prior Publication Data
US 2004/0151710 A1 Aug. 5, 2004

(51) Int. Cl.
*A01N 65/00* (2006.01)
(52) U.S. Cl. .................................... 424/725
(58) Field of Classification Search ............... 424/725
See application file for complete search history.

(56) References Cited

U.S. PATENT DOCUMENTS

| | | | | |
|---|---|---|---|---|
| 5,620,695 A | * | 4/1997 | Elliott | 424/405 |
| 5,856,364 A | * | 1/1999 | Martin | 514/724 |
| 5,858,643 A | * | 1/1999 | Ben-Hur et al. | 435/2 |
| 5,894,020 A | * | 4/1999 | Concha | 424/405 |
| 5,908,613 A | * | 6/1999 | Bozzacco | 424/50 |
| 6,045,826 A | * | 4/2000 | Borowy-Borowski et al. | 424/451 |
| 6,514,539 B1 | * | 2/2003 | Courtney | 424/725 |
| 2003/0228382 A1 | * | 12/2003 | Roth | 424/731 |

FOREIGN PATENT DOCUMENTS

| RU | 2093140 | * 10/1997 |
|---|---|---|
| RU | 2100026 | * 12/1997 |

\* cited by examiner

*Primary Examiner*—Michael Meller
(74) *Attorney, Agent, or Firm*—LaMorte & Associates

(57) ABSTRACT

A topically applied composition that is used to treat infections caused by pathogenic organisms. The composition contains *melaleuca alternifolia* extract oil to reduce the present population of the pathogenic organisms at the infection site. The composition also contains an immunostimulant that strengthens the immuno-response of the infected tissue in the area of application. The composition also includes an antioxidant that scavenges free radicals in the infected tissue and helps inhibit free radical damage. By combining these active ingredients in a carrier that can be topically applied, a composition is created that treats most every type of infection caused by pathogenic organisms with little or no side effects.

14 Claims, No Drawings

TOPICAL COMPOSITION FOR TREATING INFECTIOUS CONDITIONS OF SKIN AND MUCOSA

BACKGROUND OF THE INVENTION

1. Field of the Invention

The present invention relates to compositions used topically to treat viral, bacterial and fungal infections of the skin and mucosa. More specifically, the present invention relates to topical compositions that combine anti-microbial agents with immunostimulants and antioxidants.

2. Description of Related Art

There are many types of infectious conditions that can effect the skin and/or mucosa. Some infectious conditions are caused by bacteria, such as staph infections. Some infectious conditions are caused by viral infections, such as herpes. Still other infectious conditions are fungal in nature, such as ringworm and athlete's foot.

There are many infectious conditions that are difficult to treat. Many infections of the skin and mucosa have become resistant to common antibiotics. Viral pathogens are difficult and sometimes impossible to completely eradicate with any known medications. Furthermore, persons with many conditions, such as AIDs, chemotherapy patients, transplant patients, lupus, chronic hepatitis, alcoholic cirrhosis, leukemia, Hodgkin's disease and the like, have compromised immune systems that make treating even simple infections a complicated endeavor.

There are thousands of pathogenic organisms that can effect the skin or the mucosa. For example, athlete's foot (*tinea pedis*) can be caused by any of four pathogenic organisms. These organisms include epidermophyton floccosum, *trichophyton rubrum, candida albians* and *trichophyton mentagrophytes*. Accordingly, when a topical cream is used to treat pathogenic organisms, that cream must have an effect on a wide variety of pathogens in order to be effective.

In the prior art, there exist many compositions that are used to treat different types of pathogenic organisms effecting the skin or mucosa. Most commonly, prior art compositions are dedicated to treating a certain family of pathogenic organism, be that family viral, bacterial or fungal in nature. Few compositions have both the anti-microbial properties and anti-fungal properties needed to treat viral, bacterial and fungal infections. Of the compositions that do exist, they tend to be highly toxic to all living matter, including the living cells of body tissue. Accordingly, when topically applied, such wide-base antimicrobials and anti-fungals have a tendency to cause damage and inflammation.

Tea tree oil is the extract oil of the plant species *Melaleuca Alternifolia*. It has both antimicrobial and antifungal properties. However, its antimicrobial properties are limited. The *melaleuca alternifolia* is a shrub-like tree that is indigenous to the swampy north costal regions of Australia. The British Pharmaceutical Codex of 1949 lists *melaleuca alternifolia* as oleum melaleuca consisting of terpinenes, cymene, pinene, 1-trepinen-e-ol, cineole, sequiterpenes and sesquiterpene alcohols. Extract oil of *melaleuca alternifolia* is an oil that is extracted using a steam distillation technique. One kilogram of foliage produces between 12 grams and 25 grams of extract oil after distillation. Various compositions containing the extract oil, commonly known as tea tree oil, have been used as a topical medication for over a century.

Currently, there are United States patents that use compositions containing *melaleuca alternifolia* extract oil for the treatment of sunburn, gingivitis, and flea infestation. A typical example of the use of tea tree oil in a topical application is shown in U.S. Pat. No. 5,894,020 to Concha, entitled Soap Composition Containing Antifungal Agent, wherein tea tree oil is used to treat athlete's foot.

The present invention discloses a composition that uses tea tree oil in combination with other active ingredients that enhances the ability of the tea tree oil to effectively treat viral, bacterial and fungal infections. The result is a topical treatment that is highly effective against a wide range of infections, yet is hypoallergenic, and does not cause inflammation to the tissue when topically applied. This composition is described and claimed below.

SUMMARY OF THE INVENTION

The present invention is a topically applied composition that is used to treat infections of skin and mucosa caused by pathogenic organisms. The composition contains *melaleuca alternifolia* extract oil to reduce the present population of the pathogenic organisms at the infection site. The composition also contains an immunostimulant that strengthens the immuno-response of the infected tissue in the area of application. The composition also includes an antioxidant that scavenges free radicals in the infected tissue and helps inhibit free radical damage. By combining these active ingredients in a carrier that can be topically applied, a composition is created that treats most every type of infection caused by pathogenic organisms with little or no side effects.

DETAILED DESCRIPTION OF THE DRAWINGS

There are many types of infectious conditions that can effect the skin and mucosa. With many types of infections, the skin or mucosa may be inflamed, blistered, cracked, ulcerated or otherwise damaged by the infection. To practice the present invention, a topical composition is prepared containing *melaleuca alternifolia* extract oil (tea tree oil) in a concentration of between 0.02% and 50.0% by volume. The tea tree oil by itself is safe to use on the infection and is highly effective as an anti-fungal agent. However, the tea tree oil has limited anti-microbial properties and does little to help heal the damaged tissue after the infectious pathogen is eliminated from the skin.

To help enhance the anti-microbial properties of the tea tree oil, and to help heal damaged tissue, the tea tree oil is mixed with both an immunostimulant and an antioxidant. All of the active ingredients are then blended with a fat soluble carrier, that enables the active ingredients to be readily retained and absorbed by the skin or mucosa.

The immunostimulant is a compound that stimulates the immune system of the body to help the body produce the antibodies needed to fight the infection. An effective, non-prescription immunostimulant is Coenzyme $Q_{10}$. The chemical name for Coenzyme $Q_{10}$ is 2,3-dimethoxy-5-methyl-6-decaprenyl-benzoquinone. Coenzyme $Q_{10}$ can be produced in different ways but it is most commonly produced by cultivating a microorganism of genus *Aureobasidium* or *Trichosporon* in a culture medium containing a large quantity of p-hydroxy benzoic acid. Such a method of coenzyme $Q_{10}$ production is described in U.S. Pat. No. 4,367,288 to Kaneko, entitled Method For Producing Coenzyme $Q_{10}$.

As is discussed in U.S. Pat. No. 4,654,373 to Bertelli and in the book The Miracle Nutrient Coenzyme $Q_{10}$, by Bliznakov et al., coenzyme $Q_{10}$ has the ability to generate regrowth of damaged tissue when topically applied to damaged tissue.

Although the Coenzyme $Q_{10}$ itself does not have significant antimicrobial properties, the Coenzyme $Q_{10}$ does stimulate the immuno-response of the tissue. Accordingly, the damaged tissue is better capable of fending off infectious pathogenic organisms, such as bacteria.

The Coenzyme $Q_{10}$ is preferably added to the present invention composition in a concentration of between 0.05% and 75% by weight. When combined, the tea tree oil and the Coenzyme $Q_{10}$ have a beneficial synergistic effect. When topically applied to an area of infected tissue, the tea tree oil kills the fungal pathogenic organisms and many of the bacterial and viral pathogenic organisms that may be present. The Coenzyme $Q_{10}$ strengthens the immuno-response in the area of the infection, wherein the enhanced immuno-response enables the infected tissue to fight any remaining viral or bacterial contaminants left by the tea tree oil. Furthermore, by strengthening the immuno-response in the area of the infection, the tissue left damaged by the eradicated infection is aided in rapidly healing.

The present invention composition also contains an antioxidant. When skin or mucosa is inflamed, due to infection or trauma, arachidonic acid is produced from the phospholipid rich membranes of the skin or mucosa. The arachidonic acid causes a further inflammatory response in the skin, resulting in spreading inflammation. Arachidonic acid has a direct toxic effect on the mitochondria of cells, resulting in the uncoupling of oxidative phosphorylation. This, in turn, causes free radical damage to the mitochondrial membrane. By providing an antioxidant to the damaged tissue, the cell membranes are strengthened and the free radicals are scavenged, thereby inhibiting the free radical damage to the mitochondrial membrane.

There are many antioxidants that can scavenge free radicals in damaged cells, For example Vitamin C, vitamin A and alpha-lipoic acid can be used. However, in the present invention, Vitamin E is used as the exemplary antioxidant. The antioxidant is added to the present invention composition in a concentration of between 0.05% and 75.0% by weight.

In addition to its antioxidant effects in scavenging free radicals from tissue in and around the infection, Vitamin E provides other useful effects. Vitamin E is a natural antithrombin. The Vitamin E circulates in the blood and prevents platelet aggregation or clots from occurring inside blood vessels without adversely effecting the normal clotting process of ruptured blood vessels. It helps blood flow to the area of damaged tissue and helps accelerate healing. Similarly, Vitamin E dilates blood vessels and opens new pathways in the damaged circulatory system. Accordingly, blood flow increases to damaged tissue and the healing of the damaged tissue is accelerated.

Lastly, Vitamin E prevents the production of excessive scar tissue on the skin. As such, once the infectious pathogen is eliminated by the tea tree oil and the improved immuno-response provided by the Coenzyme $Q_{10}$, the Vitamin E acts to rapidly heal the damaged tissue and prevent scarring on the healed skin or mucosa.

Three primary ingredients of the present invention composition, therefore, serve different purposes in achieving the same goal. If a patch of tissue is infected with a fungal, bacterial or viral pathogenic organism, the infected tissue is topically treated with the present invention composition. The tee tree oil kills any fungal pathogenic organism and most of the bacterial and viral pathogenic organisms present. The Coenzyme $Q_{10}$ strengthens the immuno-response of the skin and helps the skin fight off any remaining pathogenic organisms. Lastly, the Vitamin E increases blood flow to the infected area, thereby increasing the healing rate while preventing the damaged skin from scarring.

The three active ingredients are mixed with a carrier. The active ingredients can either be dissolved in the carrier or mixed with the carrier as an emulsion. The viscosity of the carrier can cause the present invention composition to be a lotion, cream, salve, unguent, paste, gel or ointment. In the preferred embodiment, the carrier is an oil soluble material. As such, the carrier and the active ingredients mixed with the carrier will be absorbed by the fatty tissues in the skin or mucosa. This will help maintain the active ingredients at the point of application and prevent the active ingredients from being washed away by water or sweat.

One preferred carrier is olive oil. However, other vegetable oils, such as canola oil, peanut oil, corn oil or the like can be used. Olive oil is preferred because it is absorbed well by the skin and mucosa. Furthermore, olive oil has good lubricating properties that help tissue avoid chaffing against garments or bandages as the skin heals.

When the present invention composition is mixed, only effective amounts of the active ingredients are needed to treat the infected tissue. Topical applications allow the amount of compound applied to the tissue to be selectively altered to the needs of a user. For example, if a person has athlete's foot, the present invention composition can be applied twice a day, when a person normally puts on and takes off their socks. For more noticeable skin infections, such as a cold sore, the present invention composition can be applied as often as once every half hour until the sore is healed.

In tested batches of the present invention composition, tea tree oil, Coenzyme Q10, Vitamin E and olive oil were combined in different concentrations. All test batches where effective in treating skin infections caused by a variety of pathogenic organisms. In all cases, areas treated with the present invention composition healed faster than untreated areas of the same infection.

The present invention composition is intended to be topically applied to the skin or mucosa to treat infectious maladies of these tissues. The infectious malady can be fungal, viral and/or bacterial in nature. Such infectious maladies include, but are not limited to, herpes, impetigo, staph, boils, thrush, ring worm, ulcers and all secondary infections of skin wounds.

It will be understood that the present invention composition described is merely exemplary and that the ingredients can be mixed in any proportions within the ranges described. The application of the composition to skin or mucosa depends upon both the concentration of the active ingredients in the composition and the frequency at which the composition is topically applied to the infected tissue. As such, no one set concentration formulation within the described range can be considered more effective than the others. All such formulations are intended to be included within the scope of the invention as claimed below.

What is claimed is:

1. A method for treatment of an area of skin from an infection caused by bacterial, fungal or viral pathogenic organisms, said method comprising the steps of:

preparing a composition containing,
    *melaleuca alternifolia* extract oil, in an amount sufficient to suppress the pathogenic organisms;
    Coenzyme Q10 in an amount sufficient to strengthen an immuno-response in said area of skin; and
    Vitamin E in an amount sufficient to inhibit free radical damage in said area of skin; and topically applying said composition to said area of skin.

2. The method according to claim 1 wherein said composition contains from about 0.02% to about 50% by weight *melaleuca alternifolia* extract oil.

3. The method according to claim 1, wherein the composition contains between 20% and 35% by weight *melaleuca alternifolia*.

4. The method according to claim 1, wherein the composition contains from about 0.05% to about 75% by weight Coenzyme Q10.

5. The method according to claim 1, wherein the composition contains between 20% and 35% by weight Coenzyme Q10.

6. The method according to claim 1 wherein the composition contains from about 0.05% to about 75% by weight Vitamin E.

7. The method according to claim 1, wherein the composition contains between 20% and 35% by weight Vitamin E.

8. The method according to claim 1, further including a fat soluble carrier.

9. The method according to claim 8, wherein said fat soluble carrier is a vegetable oil.

10. The method according to claim 9, wherein said vegetable oil is olive oil.

11. The method according to claim 10, wherein said olive oil is between 20% and 35% by weight of the composition.

12. A method for the treatment of an infected skin area comprising topically applying to the infected skin area a composition containing *melaleuca alternifolia* extract oil, Coenzyme Q10 and Vitamin E wherein said infected skin area is infected with a pathogen selected from the group consisting of bacterial pathogens, fungal pathogens and viral pathogens.

13. The method according to claim 12, wherein said composition further includes a fat soluble carrier.

14. The method according to claim 13, wherein said fat soluble carrier is olive oil.

* * * * *